United States Patent [19]
Lee et al.

[11] Patent Number: 5,741,511
[45] Date of Patent: Apr. 21, 1998

[54] TRANSDERMAL DRUG DELIVERY DEVICE FOR TREATING ERECTILE DYSFUNCTION

[75] Inventors: Hun Han Lee; Joong Woong Cho; Choul Young Kim; Chaul Min Pai; Jin Deog Song; Chul Min Park; Hye Jeong Yoon; Yoon Yeo, all of Taejeon; Jae Seung Paick, Seoul, all of Rep. of Korea

[73] Assignee: Sam Yang Co., Ltd., Seoul, Rep. of Korea

[21] Appl. No.: 627,805

[22] Filed: Apr. 10, 1996

[30] Foreign Application Priority Data

| Apr. 12, 1995 | [KR] | Rep. of Korea | 95-8444 |
| Nov. 24, 1995 | [KR] | Rep. of Korea | 95-43422 |
| Mar. 15, 1996 | [KR] | Rep. of Korea | 96-6908 |

[51] Int. Cl.$^6$ .............................. A61F 13/00; A61F 6/02
[52] U.S. Cl. .................... 424/449; 128/842; 128/844; 600/38; 602/901; 604/347
[58] Field of Search .................... 424/449; 602/901; 128/842, 844, 918; 600/38; 604/347

[56] References Cited

U.S. PATENT DOCUMENTS

| 3,742,951 | 7/1973 | Zaffaroni | 128/268 |
| 4,573,996 | 3/1986 | Kwiatek | 604/897 |
| 4,829,991 | 5/1989 | Boeck | 128/79 |
| 5,242,391 | 9/1993 | Place et al. | 604/60 |
| 5,333,621 | 8/1994 | Denzer | 128/844 |
| 5,579,784 | 12/1996 | Harari | 128/844 |

FOREIGN PATENT DOCUMENTS

| 0 266 968 | 5/1988 | European Pat. Off. . |
| 9300894 | 1/1993 | WIPO . |

*Primary Examiner*—D. Gabrielle Phelan
*Attorney, Agent, or Firm*—Kenyon & Kenyon

[57] ABSTRACT

The present invention is to provide a method and a transdermal drug delivery device for treating erectile dysfunction which comprises a patch containing pharmaceutically active ingredient and being directly apply to the male glans penis and its support and the rings for constricting the base part of the penis to aid the erection. The patch according to the present invention may be divided into two types, i.e. a cylinder type patch and a multi-reservoir type patch. The transdermal drug delivery patch device of the present invention is painless and safely to use and may be effectively produced and maintained erection of the penis without the adverse side effects and with a high degree of patient acceptability in the case of male impotence.

9 Claims, 9 Drawing Sheets

TRANSDERMAL DRUG DELIVERY DEVICE FOR TREATING ERECTILE DYSFUNCTION

BACKGROUND OF THE INVENTION

1. Field of Invention

This invention relates to a method and a transdermal drug delivery device for treating erectile dysfunction, more specifically, a device comprising the patch applied to the glans penis of circumcised penis, the support for attaching the patch to the head of the penis said glans penis and the rings constricting the base part of the penis.

2. Description of Prior Art

It is medically well known that there are many causes of male impotence, for example, psychogenic, neurogenic, vascular, endocrine disorder or the problem of corpus cavernosa. As used herein, the term erectile dysfunction refers to certain disorders of the cavernous tissue of the penis and associated facia which produce impotence, the inability to attain a sexually functional erection; the persistent and often painful erection of the penis, a condition characterized by fibrosis of the cavernous tissue and associated painful and distorted erection of the penis.

However, in case of psychological treatment, most patient is accompanied by rejection symptoms. Internal medical and hormone therapy are likely to cause side effects. The vacuum tumescence device may have an inconvenience and trouble in using the jelly and device. The artificial erection method using the penile prosthesis, reconstruction of corpus cavernosum arteria and vein ligation are accompanied with fear on the surgical operation. In case of self-injection method of vasodilating agents, continuous treatment is difficult on account of pain at injection, rejection symptoms on injection and fibrosis of injection portion.

With respect to administration of drugs directly to the penis, medicated catheters such as described in U.S. Pat. No. 4,640,912 have been used to prevent or treat localized infections and irritation of the urethra and bladder; a nitroglycerin coated, erection inducing condom is disclosed in U.S. Pat. No. 4,829,991; the transurethral administration of certain drugs is suggested in U.S. Pat. Nos. 4,478,822, 4610,868, 4,640,912 4,746,508, 5,242,391; and medicated urethral suppositories, inserts or plugs, typically containing anti-infective agents or spermicides are disclosed in U.S. Pat. Nos. 1,897,423, 2,584,166, 2,696,209 and 3,373,746, for example.

As conventional pharmaceutical formulation, spray formulation, ointment and urethral insertion formulation have been used.

However, the urethral insertion formulation made by dispersing the drug in the high molecular hydrogel is an erection-producing formulation by inserting hydrogel containing a drug into the urethra. In case of this formulation, there exists a trouble in using a special device in order to insert hydrogel into the urethra. In particular, there is serious apprehension about infection during the treatment, and the weak mucous membrane of urethra is easily infected.

Furthermore, a conventional spray formulation or ointment is an erection-producing formulation by applying or spraying the drug onto the penile shaft or glans. However, such formulation cannot maintain a sufficient erection which is necessary for sexual intercourse when the anatomic structure of the penis is observed.

There are many patents describing devices for administration drugs through the skin; U.S. Pat. Nos. 3,598,122; 3,598,123; 3,742,951; 4,031,894; 4,060,084 ;4,144,317; 4,201,211 and 4,379,454.

Such transdermal drug delivery devices are commonly in the form of a laminated composite that includes a reservoir layer containing the drug, a pressure sensitive adhesive layer for attaching the composite to the skin, and a backing layer that forms the upper layer of the device. Depending upon the particular drug and drug formulation involved, the reservoir layer may be a matrix in which the drug formulation is dispersed or a layer in the form of a walled container which holds the drug formulation. Container type reservoirs are often formed as a pocket between the backing layer and drug-permeable basal membrane through which the drug passes to the skin.

U.S. Pat. No. 5,333,621 combines a conventional condom with transdermal delivery device having a vasodilator for generating the erection of the penis for sexual intercourse. The transdermal medication device delivers the vasodilator especially to the skin surface of penile shaft.

The penis is composed of three cylindrical masses of erectile tissue, the dorsally paired corpora cavernosa and the unpaired corpus cavernosum urethrae. Each corpus cavernosum is surrounded by a dense capsule or tunica albuginea composed of collagenous fibers.

As can be seen from the said anatomic structure of the penis, the penile shaft of the penis using a patch in U.S. Pat. No. 5,333,621 cannot deliver the drug to the corpus cavernosum through the tunica albuginea which is a fibrous tough collagen membrane having a thickness of 0.5 to 2.2mm. Therefore, the patch device disclosed in the above Pat. No. is nothing but a simple formulation disregarding the anatomic structure of the penis.

In other words, a patch disclosed in U.S. Pat. No. 5,333,621 is nothing but a common system by simply combining a patch with the condom for applying it to the penile shaft without considering any special method or means to maximize or increase the penetration of the drug through the tunlea albuginea. Furthermore such patch with a condom may cause the side effects including allergy due to the condom to the male as well as the female, and may not give the orgasm during the sexual intercourse. Therefore, such patch system may not apply to the persons having the rejection symptoms on the use of condom.

The glans penis of the penis practically has no tunica albuginea which is a main barrier for inhibiting the penetration of drug through the skin contrary to the penile shaft in view of anatomic aspect, and has only fibrous tissue between sinusoid and epidermis.

The present invention is characterized in that a patch is applied directly to the glans penis to deliver the drug to the corpus cavernosum, thereby providing a patch device for treating the erectile dysfunction.

SUMMARY OF THE INVENTION

The object of the present invention is to provide a method and device for treatment of erectile dysfunction which are painless, safely and effectively producing erection of the penis without the adverse side effects and with a high degree of patient acceptability in the case of male impotence.

The another object of the present invention is to provide a transdermal drug delivery device for treating erectile dysfunction comprising the cylinder or multi-reservoir type patches applied to the glans penis in circumcised penis, the condom type or an adhesive band type support for attaching the patch to the glans, and rings constricting the base part of the penis body.

First characteristic of the present invention is to apply the patch device to the glans penis in circumcised penis, where the glans is appropriate site for absorbing the drugs because the glans penis has practically no tunica albuginea and only a minimal amount of fibrous tissue between the sinusoid and epidermis.

Second characteristic of the present invention is the shape of the patch device classified into two types, a cylinder type and multi-reservoir type patches. Furthermore multi-reservoir type patch said container type reservoir comprises multiple reservoirs containing pharmaceutically active drugs.

Further functional characteristic of multi-reservoir type patches are delivering the various compositions of medication by inserting different drugs to each reservoir and convenience of attaching the patch to the glans due to its flexibility.

Third characteristic of present invention is the rings constricting the base part of the penis body, consisting of two rings having different constricting power, one of which shall be removed before the sexual intercourse.

REFERENCE NUMERAL

20 Multi-reservoir type patch I, 21 Release liner, 22 Rate control membrane, 23 Backing layer, 24 Reservoir layer, 25 Space between multiple reservoirs, 26 Fist heat-sealing region, 27 Second heat-sealing region, 28 Adhesive band type support, 29 Adhesive layer, 30 Constricting ring I, 40 Constricting ring II, 41 Magic tape type constricting ring, 42 Hook type Constricting ring, 43 Hold elastic type Constricting ring, 44 Silicon oil insertion type constricting ring, 44 air insertion type constricting ring, 60 Multi-reservoir type patch II, 70 Release liner, 100 Cylinder type patch, 101 Backing layer, 102 Reservoir layer, 103 Rate controlling membrane, 104 Release liner, 200 Condom type support, 201 Backing layer, 202 Matrix layer, 203 Release liner, 401 Elastic band, 402 Negative part of magic tape, 403 Positive part of magic tape, 404 Hold elastic band, 405 Hold part, 406 Hook, 407 Insert silicon oil or air, 408 Oil inserting hole.

DETAILED DESCRIPTION OF THE INVENTION

In reference to the drawings, the present invention can be explained in detail.

Figure 1:
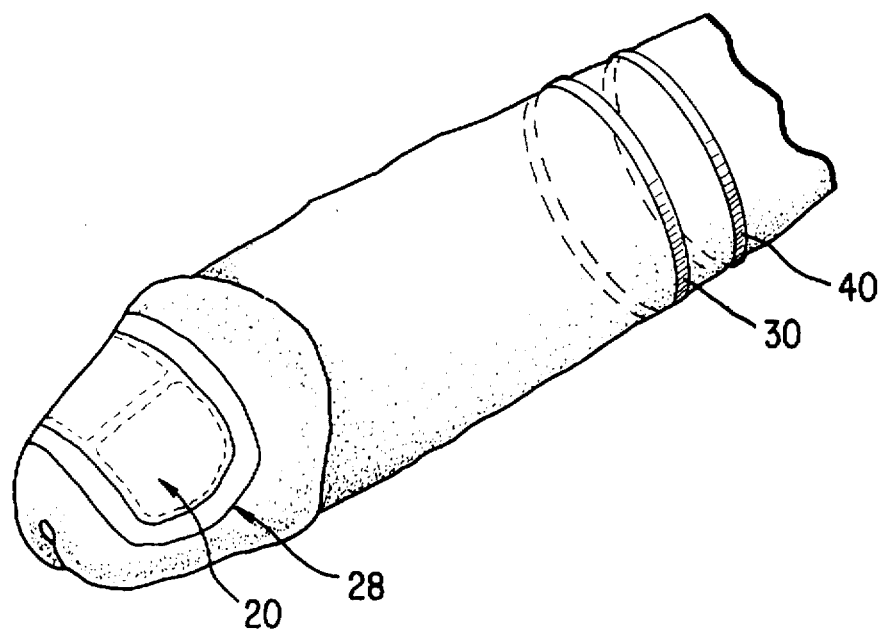
FIG. 1 is a perspective view applied multi-reservoir type patch device of the present invention to glans penis in the circumcised penis.

As shown in FIG. 1, the multi-reservoir type patch device of the present invention comprises a multi-reservoir type patches(20, 60) applied to the glans penis of the circumcised penis, an adhesive band type support(28) for attaching the patch to the glans and two constricting ring(30, 40) for constricting the base part of the penis body.

Figure 2:
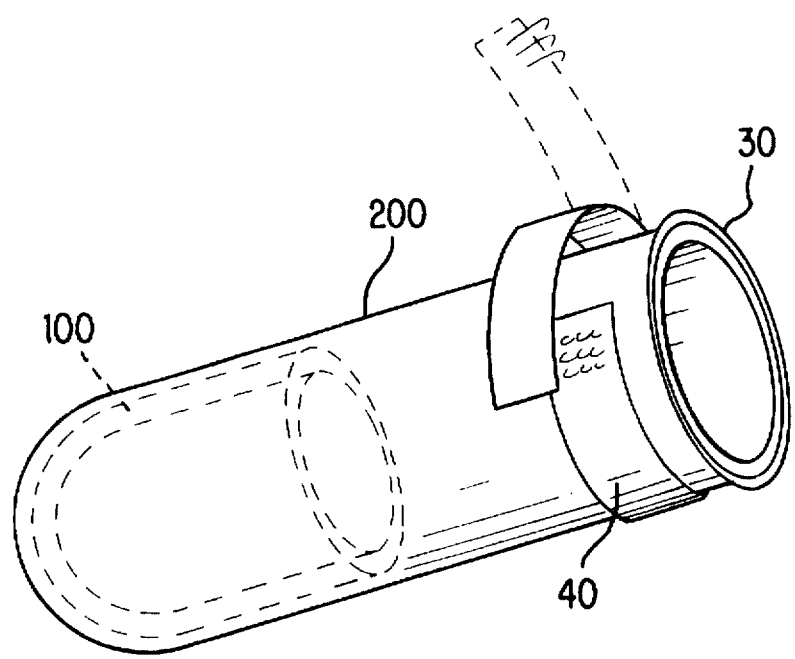
FIG. 2 is a schematic view of the cylinder type patch of the present invention.

As shown in FIG. 2, the cylinder type patch device of the present invention comprises a cylinder type patch(100), a condom type support(200) having constricting ring I(30) in the entrance of condom and a constricting ring II(40) for constricting the base part of the penis.

Figure 2A:
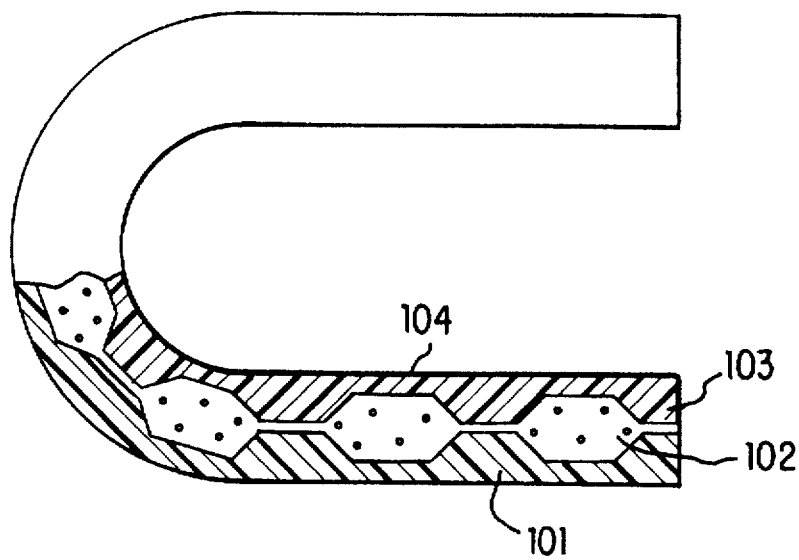
FIG. 2(A) is a cross-sectional view of cylinder type reservoir patch in FIG. 2.
Figure 2B:
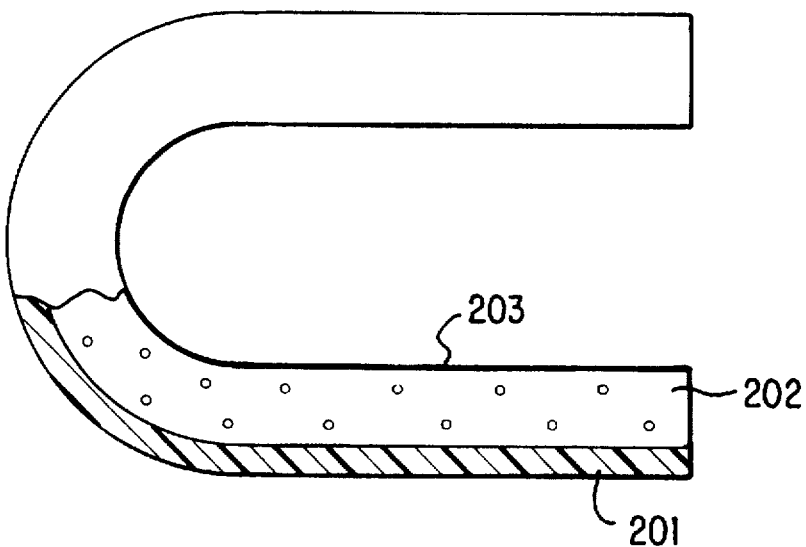
FIG. 2(B) is a cross-sectional view of cylinder type matrix patch in FIG. 2.

FIG. 2(A) and FIG. 2(B) show the cross-sectional views of reservoir patch and matrix patch of cylinder type, respectively.

Referring to FIG. 2(A), the reservoir patch of cylinder type consists of a drug and light impermeable backing layer(101), a reservoir layer containing pharmaceutically active drugs(102), a rate controlling membrane(103) of drug release, and a release liner(104) to be removed before use. More specifically, the backing layer(101) is made by polyester film or polyester film coated with aluminum membrane impermeable to drugs and light. The rate controlling membrane(103) is characterized in dense or microporous membrane controlling drug release rate to the skin. The material of release liner(104) is same as that of backing layer.

Referring to FIG. 2(B), this matrix patch of cylinder type consists of a drug and light impermeable backing layer(201), a polymer matrix containing medication(202), and a release liner(203) to be removed before use. The polymer matrix (202) is attached to the glans penis of the circumcised penis.

Figure 3:
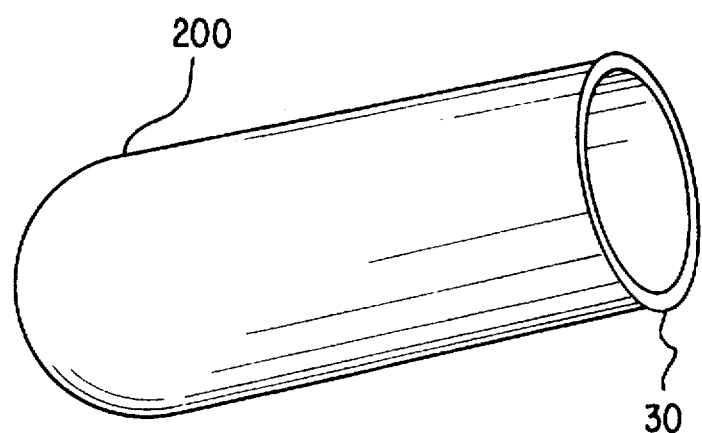
FIG. 3 is a schematic view of the condom type support and a constricting ring of the cylinder type patch device.
Figure 4A:
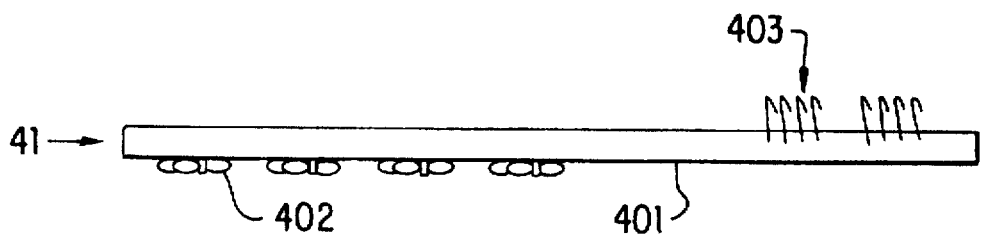
FIG. 4 shows the various types constricting rings of the present invention.
Figure 4B:
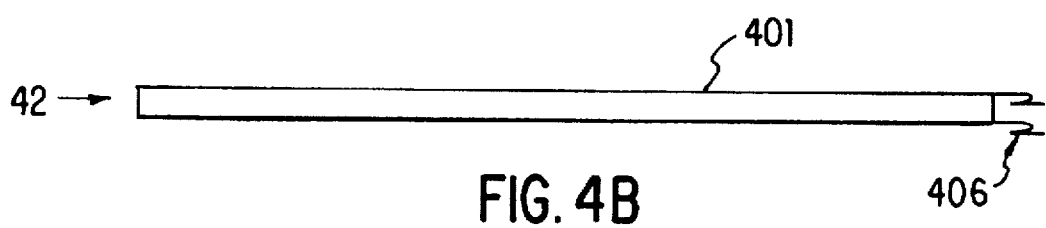
Figure 4C:
Figure 4D:
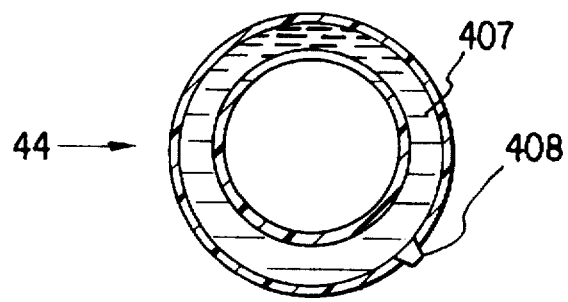

As shown in FIG. 3, the condom type support(200) fixes the patch to the glans penis of the circumcised penis. The material of supporter is selected from elastomer, polyurethane and natural or synthetic rubber. Further, the constricting ring(30) exists in the entrance of condom type support (200) in order to assist penile erection.

FIG. 4 shows the various types of constricting rings(40) used in this invention. The types of constricting rings are magic tape type(41), hook type(42), hold elastic type (43) and silicon oil insertion type (44), or air insertion type (44). Among them, silicon oil insertion(44) or air insertion type (44) is more effective and convenient ring for use. It is generally required two constricting rings to assist penile erection of the penis. During the penile erection, one of two rings is removed before sexual intercourse.

Figure 5A:
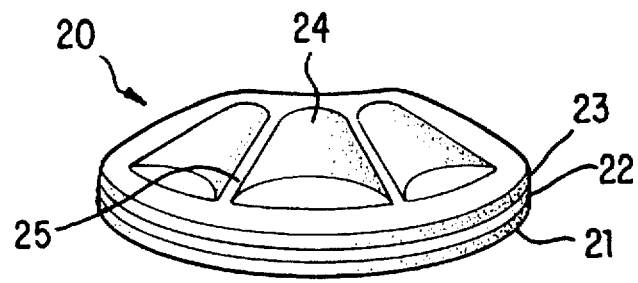
FIG. 5(A) is a perspective view of one multi-reservoir type patch of the present invention.
Figure 5B:
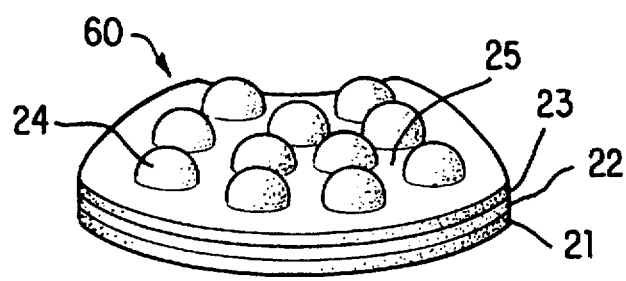
FIG. 5(B) is a perspective view of another multi-reservoir type patch of the present invention.
Figure 6:
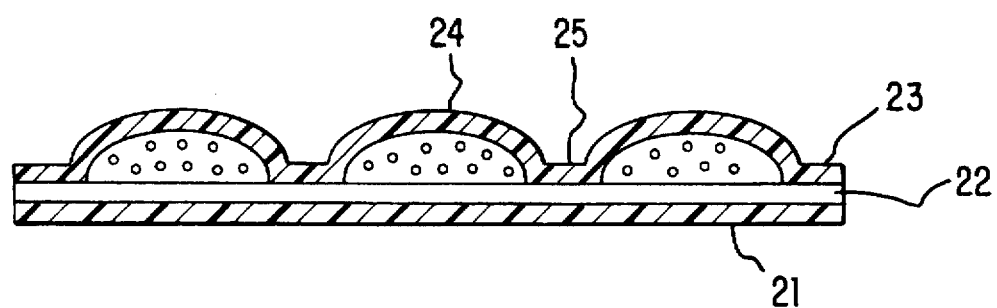
FIG. 6 is a cross-sectional view of a multi-reservoir type patch of figure 5(A).

FIG. 5(A) and FIG. 5(B) show two types of multi-reservoir patch. As shown in these figures, multi-reservoir type patch consists of multiple reservoirs containing pharmaceutically active drugs, a drug impermeable release liner (21), a rate control membrane(22) for controlling the drug release rate, multiple reservoirs layer(24) containing medication, and a drug impermeable backing layer(23). There exist heat-sealing spaces(25) among multiple reservoirs where the patch can be easily bent due to heat-sealing space between multiple reservoirs. Using these heat-sealing spaces(25), the patch can be easily attached to the conically shaped glans. The structure of multi-reservoir type patch is shown in FIG. 6 in more detail.

Figure 7:
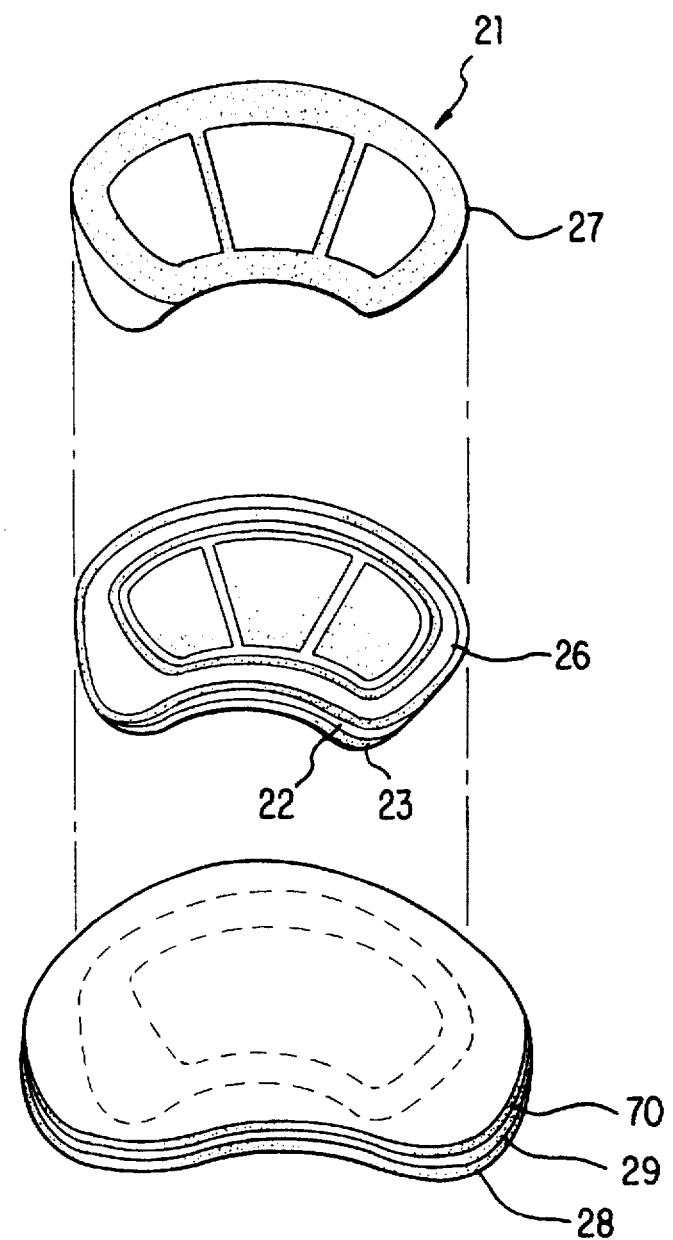
FIG. 7 is a schematic view separating the components of multi-reservoir type patch device in FIG. 5(A).

FIG. 7 shows a schematic view super imposing the components of multi-reservoir type patch device in FIG. 5(A).

An adhesive band type support(28) coated with pressure sensitive adhesive(29) is used for attaching the multi-reservoir type patch to the glans penis of the circumcised penis. Release liner(70) is removed just before using this the support(28).

The method for manufacturing the multi-reservoir type patch device of the present invention can be described as follows.

The drug impermeable backing film is laid on the mold having multiple reservoirs shape. Using vacuum, the backing film is formed as multi-reservoir shape with heat-treatment. The drug is loaded in the multiple reservoirs before the first heat-sealing with the rate controlling membrane. The second heat-sealing is carried out upon laying the release liner to the rate controlling membrane.

There are two characteristics in the multi-reservoir type patch.

One is to deliver the various compositions of medication by inserting different drugs to each reservoir. It is possible to get multiple administration effect by each reservoir, where compose of different drug medication. The other is the convenience of attaching the patch to the conically shaped glans, because the heat-sealing spaces among multiple reservoirs let it bent easily for attachment.

Use of transdermal drug delivery device for treatment erectile dysfunction of the invention is as follows. The penile erection is induced by attaching the patch to the glans penis of the circumcised penis with support and two rings; one ring is removed during penile erection. After achieving enough erection, the patch and support are removed just before the sexual intercourse ; and having sexual intercourse with only one ring.

The drugs applied to the patch for penile erection are as follows.

In general, vasodilators, smooth muscle relaxants, alpha-blockers, dopamine agonists, opioid agonists, potassium channel opener, calcium blockers, alpha-adrenalin agonists, bronchodilators, specific phosphodiesterase III inhibitors and/or vasoactive intestinal peptides can be applied.

More specifically, phenoxybenzamine, dibenamine, doxazosin, terazosin, phentolamine, tolazoline, halperidol, adenosine, ergot alkaloids, chlorpromazine, yohimbin and/or verakpamil can be used as alpha-blockers.

Ditiazem, nifedipine, nicardipine, nimodipine and/or verapamil can be used as calcium blockers. Further, PGE1, alprostadil, misoprostol and/or PGE2 as natural and synthetic vasoactive prostaglandins; apomorphine, bromocriptine as dopamine antagonists; adenosine, amylnitrate, dipyridamole, erythrityl tetranitrate, ethaverine hydrochloride, isosorbide dinitrate, isoxsuprine hydrochloride, milrinone lactate, niacine, niacinamide, nicotinyl alcohol, nitroglycerin, nylindrin hydrochloride, papaverine hydrochloride, pentaerythritol tetranitrate, pentaerythritol phenobarbital, pentoxyfylline, pinacidil, sodium fluroride and/or tolaxoline hydrochloride as vasodilating agents can be used.

Aminophylline, amobarbital, ephedrine aminohylline, ephedrine, phenobarbital, potassium iodide aminophylline, guaifenesin sminophylline, potassium iodide butabarbital, pseudoephedrine, theophylline dextrose, theophylline dyphylline, hydroxazine hydrochloride, iodinated glycerol and/or theophylline anhydrous can be used as smooth muscle relaxants.

The effect of the transdermal drug delivery device of this invention can be described with following examples.

Composition of Applied Medicine

Prostaglandin EI(PGE1) was used as an active ingredient. 10–70 weight % of enhancer selected from C10–C18 fatty acid or fatty alcohol and 20–40 weight % of triacetin as stabilizer were included in the composition.

Application to the Patients or Volunteers

For the human application of transdermal drug delivery device of the present invention, erectile dysfunction patients and patients under the spinal anesthesia were selected. Spinal anesthetic patients were selected for removing the mental effects occurred by conscious patients during the experiment.

Rigiscan was used for measuring the rigidity and circumference change of the penis. During the experiment, audio-visual sexual stimulation was given to the patients or volunteers continuously.

COMPARATIVE EXAMPLE

Application to Two Constricting Rings Without Patch

Two constricting rings without patch were applied to the patient under the spinal anesthesia.

The rigidity and circumference change of the penis especially at the tip and base part of the penis body was measured with two rings.

Figure 8A:
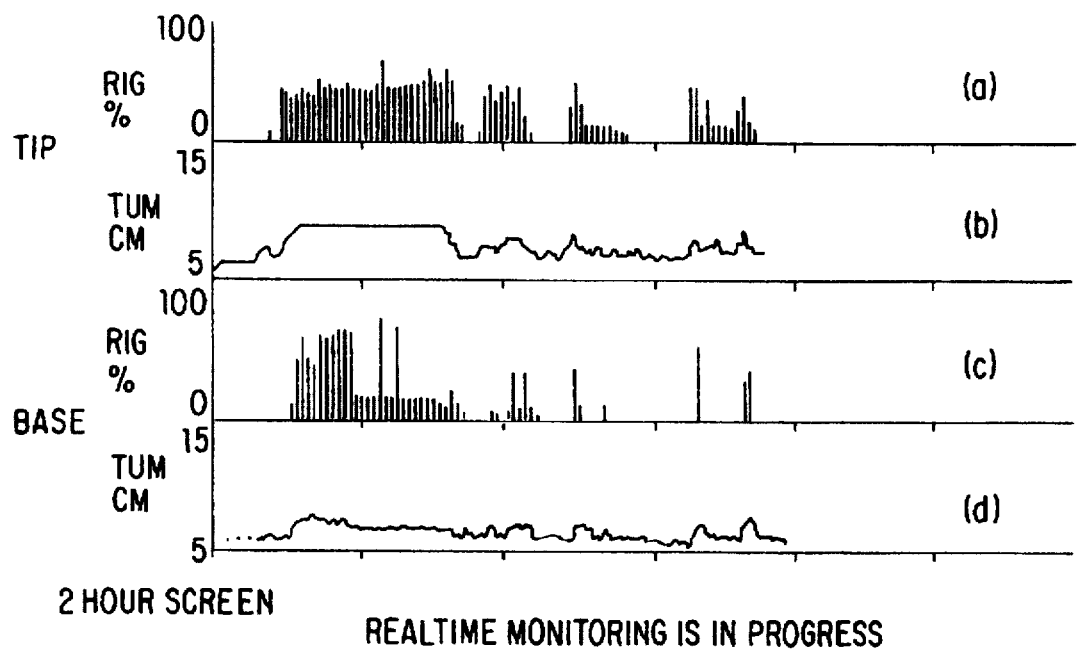
FIG. 8(A) is the graphs measured by rigiscan showing the rigidity and circumference change of the penis only applied to two constricting rings.

FIG. 8(A)—(a) showed the changes of rigidity at the tip part of the penis. During 20 to 50 minutes, the rigidity was approximately 30 to 40 percentages. After removing one restricting ring at 40 minutes, the rigidity of the penis was suddenly declined. The circumference change of the tip part of the penis was shown to FIG. 8(A)—(b).

In initial stage, the circumference changed from 5 cm to 7–8 cm for 10–35 minutes. Then, the circumference declined irregularly.

Figure 8B:
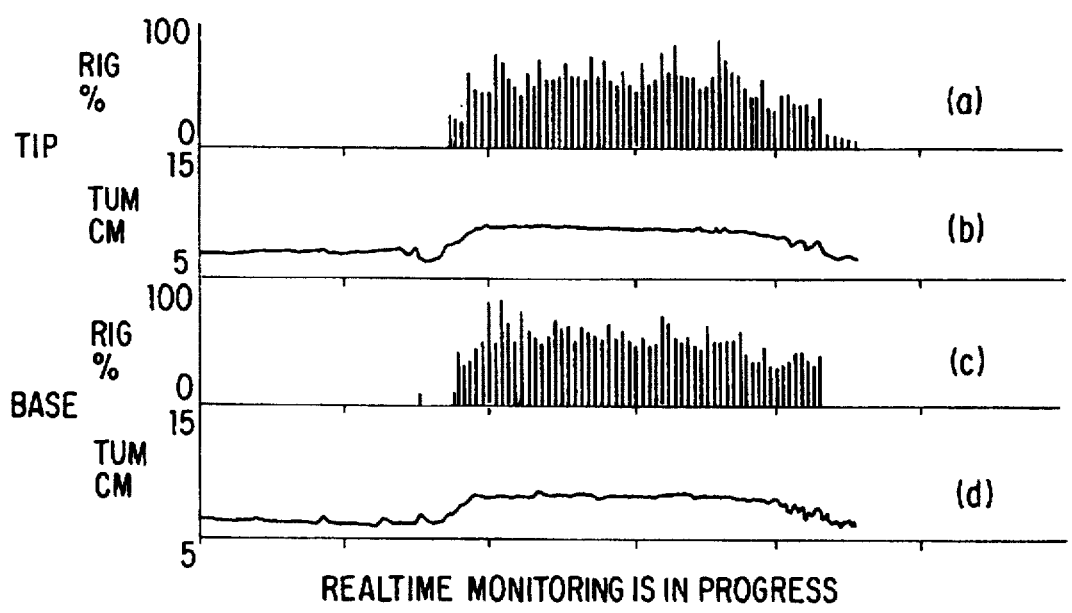
FIG. 8(B) is the graphs measured by rigiscan showing the rigidity and circumference change of the penis only applied to our invention patch device and two constricting rings.

FIG. 8(A)—(c) showed the change of rigidity at the base part of the penis. For 10–20 minutes, 40—50% of rigidity was shown. After 20 minutes, the rigidity declined suddenly. Then circumference changes at the tip part of the penis show irregular small change in FIG. 8(A)—(c).

As a conclusion, application two rings to volunteer could not solve the erectile dysfunction, because the base part of the penis did not show enough rigidity for sexual intercourse.

Application to Only Multi-Reservoir Type Patch

A multi-reservoir type patch was applied to the patient under the spinal anesthesia.

Multi-reservoir type patch containing medication was attached to the glans penis using an adhesive band type support. After a lapse of 40 minutes, enough erection was not detected for sexual intercourse. Applying only multi-reservoir type patch could not solve the erectile dysfunction.

EXAMPLE

Application to Multi-Reservoir Type Patch With Two Constricting Rings to the Volunteer Multi-reservoir type patch containing medication with two constricting rings was applied to the patient under the spinal anesthesia.

As shown in FIG. 8(B)—(a), 60–80% of constant rigidity were measured at the tip part of the penis for 35–90 minutes. The circumference change showed from 6cm to 8–9cm for 40–90 minutes as shown in FIG. 8(B)—(b).

At the base part of the penis, 60–80% of rigidity was shown for 35–90 minutes in FIG. 8(B)—(c). Further, the circumference change showed from 6cm to 7–9cm for 40–90 minutes.

Therefore, as shown in FIG. 8, sufficient rigidity and circumference changes were measured at the tip and the base of the penis for sexual intercourse.

As a conclusion, the multi-reservoir type patch with two constricting rings was required for sufficient penile erection.

The drug penetrated glans transferred to the corpus cavernosa through the erectile tissue and small veins. Migration time of sufficient drug to the corpus cavernosa was required 40 minutes. During this time, two constricting rings delay the drug loss as the blood flows through the superficial emissary vein.

As described in above, the transdermal drug delivery patch device for treating erectile dysfunction according to the present invention may be produced and maintained sufficient erection and rigidity for sexual intercourse. Furthermore, in case of using the patch device of the invention, it may be overcome pain and trouble by injection and there is not serious apprehension about infection and wound occurrence of the weak mucous membrane of urethra during the treatment.

Application to Multi-Reservoir Type Patch With Two Constricting Rings to the Impotence Patient During 40 minutes, the rigidity at the tip and the base of the penis was measured in 20–30%. After a lapse of 40 minutes, the rigidity of the penis was suddenly induced at the moment of cutting one ring. After one hour, 60–70% of rigidity enough to sexual intercourse were shown. Therefore, the device comprising a patch, an adhesive band type support and two rings was appropriate for enough penile erection.

We claim:

1. A transdermal drug delivery device for treating erectlie dysfunction which comprises:
   a) a transdermal multi-reservoir patch containing a drug for treating erectlie dysfunction for application to the glans of a circumcised penis and two separated rings for placement at or near the base of the penis body, each of said rings having different constricting power; and
   b) an adhesive band for attaching the patch to the glans of the circumcised penis;
   wherein the separated rings constrict the base part of the penis body, thereby controlling venous outflow and drug loss.

2. The transdermal drug delivery device for treating erectile dysfunction according to claim 1, wherein the multi-reservoir patch consists essentially of a drug impermeable release liner (21), a rate controlling membrane (22) for controlling drug release, reservoir layer containing the drug (24), and a drug impermeable backing layer.

3. The transdermal drug delivery device for treating erectile dysfunction according to claim 1, wherein the multi-reservoir type patch comprises reservoirs formed between the backing layer and rate controlling membrane.

4. The transdermal drug delivery device for treating erectile dysfunction according to claim 2, wherein the multi-reservoir patch comprises heat-sealing space between the reservoirs, thereby allowing easy attachment of the patch to the glans.

5. The transdermal drug delivery device for treating erectile dysfunction according to claim 1, wherein the constricting rings are selected from the group consisting of tape rings (41), hooks (42), hold elastic rings (43) and silicon oil insertion rings.

6. A process for manufacturing the multi-reservoir patch device of claim 5, comprising the steps of:
   a) laying the drug impermeable backing layer on a mold having a reservoir shape;
   b) forming the backing layer into multiple reservoirs using a vacuum and heat treatment;
   c) loading the drug in the multiple reservoirs before heat-sealing thereon the rate controlling membrane; and
   d) heat-sealing the release liner onto the rate controlling membrane.

7. A method for treating erectile dysfunction of a circumcised patient which comprises administering a therapeutic amount of an agent effective for said erectile dysfunction, said method comprising the steps of
   1) inducing penile erection by adhesively attaching a transdermal multi-reservoir patch containing a therapeutic agent for treating erectile dysfunction to the glans and attaching two constricting rings at or near the base of the penis; and
   2) removing the transdermal multi-reservoir patch and one ring after penile erection is obtained and prior to sexual intercourse.

8. The method for treating erectile dysfunction according to claim 7, wherein the erectile dysfunction is impotence and the therapeutic agent is selected from the group consisting of vasodilators and alpha-blockers.

9. The method for treating erectlie dysfunction according to claim 7, wherein said therapeutic agent is selected from the group consisting of phentolamine, prostaglandin E1 papaverine and analogues thereof.

* * * * *